US008751255B2

(12) United States Patent
Brown (10) Patent No.: US 8,751,255 B2
(45) Date of Patent: Jun. 10, 2014

(54) SYSTEMS AND METHODS FOR DELIVERING ON-CALL DATA FOR HEALTH CARE LOCATIONS AND PHYSICIANS

(76) Inventor: Curtis W. Brown, Reno, NV (US)

(*) Notice: Subject to any disclaimer, the term of this patent is extended or adjusted under 35 U.S.C. 154(b) by 635 days.

(21) Appl. No.: 12/437,453

(22) Filed: May 7, 2009

(65) Prior Publication Data
US 2009/0292555 A1 Nov. 26, 2009

Related U.S. Application Data

(60) Provisional application No. 61/055,348, filed on May 22, 2008.

(51) Int. Cl.
G06Q 10/00 (2012.01)
G06Q 40/00 (2012.01)
G06Q 50/00 (2012.01)
G06F 19/00 (2011.01)

(52) U.S. Cl.
USPC .................................................. 705/2; 705/3

(58) Field of Classification Search
USPC .......................................................... 705/2
See application file for complete search history.

(56) References Cited

U.S. PATENT DOCUMENTS

| | | | |
|---|---|---|---|
| 6,944,536 B2* | 9/2005 | Singleton | 701/209 |
| 7,249,036 B2 | 7/2007 | Bayne | |
| 7,912,733 B2* | 3/2011 | Clements et al. | 705/2 |
| 2002/0103691 A1 | 8/2002 | Smith | |
| 2002/0103692 A1 | 8/2002 | Rosenberg et al. | |
| 2002/0165732 A1 | 11/2002 | Ezzeddine et al. | |
| 2002/0191035 A1 | 12/2002 | Selent | |
| 2003/0149598 A1 | 8/2003 | Santoso et al. | |
| 2004/0148194 A1* | 7/2004 | Wellons et al. | 705/2 |
| 2006/0015369 A1* | 1/2006 | Bachus et al. | 705/2 |
| 2006/0031109 A1 | 2/2006 | LaRue, Jr. et al. | |
| 2006/0195339 A1 | 8/2006 | Backhaus et al. | |
| 2007/0136095 A1 | 6/2007 | Weinstein | |
| 2007/0150311 A1* | 6/2007 | Lazerus | 705/2 |
| 2008/0059268 A1 | 3/2008 | Davantes et al. | |
| 2009/0125326 A1* | 5/2009 | Wasson et al. | 705/2 |

OTHER PUBLICATIONS

Green et al., "On-Call Physicians at California Emergency Departments: Problems and Potential Solutions", California HealthCare Foundation, Jan. 2005, pp. 1-15.
Hamilton, Thomas E., "Revised Emergency Medical Treatment and Labor Act (EMTALA) Interpretive Guidelines", Centers for Medicare & Medicaid Services, May 13, 2004, pp. 1-2, 19-25 and 49-50.
Hamilton, Thomas E., "Revisions to Special Responsibilities of Hospitals under the Emergency Medical Treatment and Labor Act (EMTALA)", Centers for Medicare & Medicaid Services, Sep. 29, 2006, pp. 1-2.

(Continued)

Primary Examiner — Hiep V Nguyen
(74) Attorney, Agent, or Firm — Knobbe, Martens, Olson & Bear, LLP (57) ABSTRACT

A system which contains real-time specialist on-call data is disclosed. The system allows for the input and searching of specialist on-call data for various health care locations. The system is configured to allow a patient in need of the medical care of a specialist not currently available at the patient's location to search for the nearest health care location(s) with a physician of the desired specialization presently or soon to be on call. Methods of the same are also disclosed.

37 Claims, 8 Drawing Sheets

(56) References Cited

OTHER PUBLICATIONS

American College of Emergency Physicians, "EMTALA and On-call Responsibility for Emergency Department Patients" on worldwide web page for acep.org, printed on Mar. 8, 2009.

Seay et al., "Availability of On-Call Specialists—an Information Paper", American College of Emergency Physicians, May 2005, pp. 1-9.

Vanlandingham et al., "ACEP Survey of Emergency Department Directors", American College of Emergency Physicians, Apr. 2006, pp. 1-7.

Homeland Security Presidential Directive, Oct. 18, 2007 (online) http://www.fas.org/irp/offdocs/nspd/hspd-21.htm 9 pages.

Menchine, Michael D., MD, Mph et al. "On-call Specialists and Higher Level of Care Transfers in California Emergency Departments", Society for Academic Emergency Medicine, 2008, pp. 329-336.

Sasser, Scott M., et al. "In a Moment's Notice: Surge Capacity for Terrorist Bombings is a publication of the National Center for Injury Prevention and Control, Centers for Disease Control and Prevention", Centers for Disease Control and Prevention, 2007, 60 pages.

* cited by examiner

![Screenshot of FINDONCALLMD.COM Calendar of Coverage page]

Organization 800

FINDONCALLMD.COM
Emergency Transfer Help

- Home
- Hospitals on Call
- Calendar
- Related Links

Calendar of Coverage

Cardiology (CARD)
ENT (ENT)
Family Medicine (FM)
Gastroenterology (GI)
General Surgery (SURG)
Nephrology (NEPH)
Pediatric Surgery (PS)
Pediatric Cardiology (PC)

Always open for acute strokes

Always open for TRAUMA

| April 2008 | | | | | | |
|---|---|---|---|---|---|---|
| Sun | Mon | Tue | Wed | Thu | Fri | Sat |
|  |  | 1 Card ENT | 2 Card ENT | 3 Card ENT | 4 Card ENT | 5 Card ENT |
| 6 Card ENT | 7 Card ENT | 8 Card ENT | 9 Card ENT | 10 Card ENT | 11 Card ENT | 12 Card ENT |
| 13 | 14 | 15 | 16 | 17 | 18 | 19 |
| 20 PS PC | 21 PS PC | 22 PS PC | 23 PS PC | 24 PS PC | 25 PS PC | 26 PS PC |
| 27 | 28 | 29 | 30 |  |  |  |

Happy Hope Hospital
999-999-9992
123 Fast Pitch Road
No Where, Nevada

810

805

Our hospital is a Stroke Center and would welcome all acute strokes.

TRAUMA CENTER LEVEL II

Home | Product List | Calendar | Related Links

SYSTEMS AND METHODS FOR DELIVERING ON-CALL DATA FOR HEALTH CARE LOCATIONS AND PHYSICIANS

CROSS-REFERENCE TO RELATED APPLICATIONS

This application claims priority under 35 U.S.C. §119(e) to U.S. Provisional Application Ser. No. 61/055,348, filed on May 22, 2008, titled "SYSTEMS AND METHODS FOR DELIVERING ON-CALL SCHEDULE DATA FOR HOSPITALS AND PHYSICIANS", the entire disclosure of which is hereby expressly incorporated herein by reference.

BACKGROUND

1. Field

The field of the disclosure relates generally to improving the speed and efficiency with which a health care facility currently having a doctor or physician with a particular specialty on-call may be located and identified.

2. Description of the Related Art

Currently there is no centralized database or data bank which assists in finding specialists on a real-time basis to care for patients requiring emergency care. In general, if a hospital does not or cannot provide an emergency service which is required for a patient, then the hospital must, and may be legally obligated to, arrange for the patient to be transferred to a facility which can provide that care immediately. For example, in certain situations, the federal Emergency Medical Treatment and Active Labor Act (EMTALA) or other state or federal law may require a hospital to transfer a patient who comes to its emergency department suffering from an emergency medical condition to another hospital able to treat the patient. Searching for a hospital with a physician of a desired specialization to treat the emergency medical condition currently on call is now often done manually, where the hospital telephonically calls up hospitals in an attempt to identify another hospital or care facility with the required specialist currently on call. It can take an enormous amount of time and effort to locate such an alternate facility which can provide the needed care, and this lost time may be wasted to the detriment or death of the patient.

SUMMARY

A database or data bank which contains real-time data of health care facilities or hospitals with physicians of a particular specialty that are on-call is disclosed. In some embodiments, the database may be accessible through the Internet and can be available to health care providers 24 hours a day. A website may provide access to the database and provide information as to the nearby locations of the appropriate institutions and care givers for a given specialty. In various embodiments, the information may include hospital names, physician names, locations, phone numbers, distance from a requester's (or any given) location, and maps to identified facilities. In some embodiments, additional information may include transportation options for transporting the patient to the identified alternate facility, providers and hospitals requesting referrals and regional centers, etc.

DETAILED DESCRIPTION OF PREFERRED EMBODIMENTS

The following detailed description is directed to certain specific embodiments of the invention. However, the invention can be embodied in a multitude of different ways.

Figure 1:
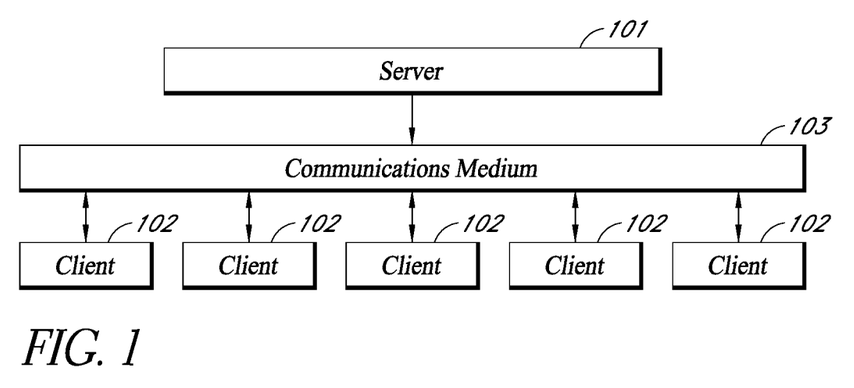
FIG. 1 illustrates an embodiment in which a server communicates with multiple clients over a communications medium, such as the Internet.

FIG. 1 illustrates a server computer system 101 communicating with multiple client computer systems 102 over a communications medium 103, such as the Internet. The server 101 can include one or more server computer devices with a machine-readable queriable database or data bank of on-call schedule information for doctors and health care facilities. The clients 102 can be configured to query the server's 101 database by use of, e.g. web browsers.

Figure 2A:
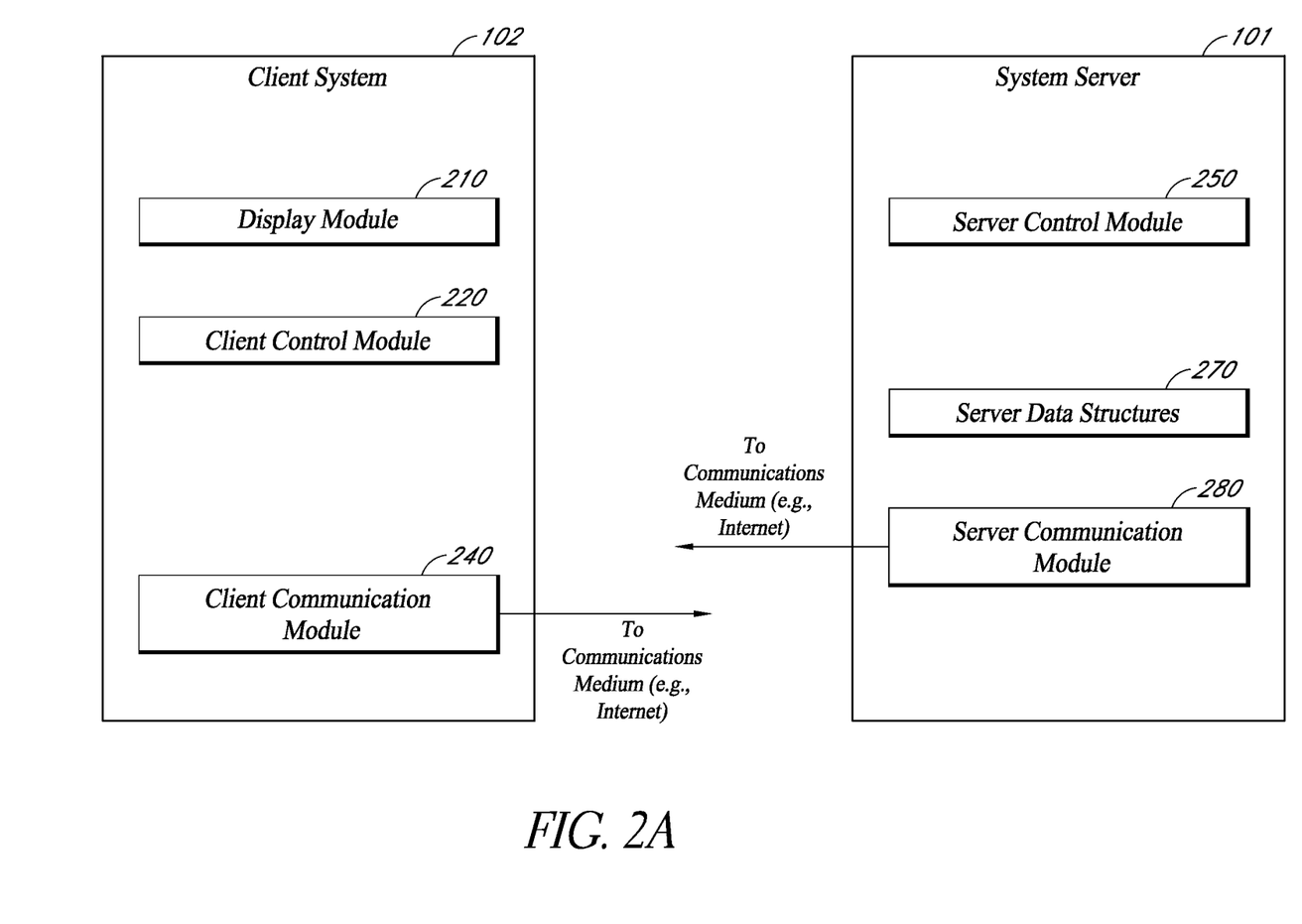
FIG. 2A schematically depicts the structures of the client and server according to one embodiment of the invention.

FIG. 2A schematically depicts the structures of the client 102 and server 101 according to one embodiment of the invention. The client system 102 may contain a display module 210 and a client control module 220. The client 102 display module 210 and control module 220 may comprise a web browser to allow the client to interface with the server 101 over a communications medium, such as the Internet. Although not illustrated in FIGS. 1 and 2A, the server computer system 101 and the client computer system 102 may comprise various components typically included in a computer system, such as CPU, disk memory or other memory, RAM, network interfaces, peripheral device interfaces, etc.

The server system 101 may also comprise a server 101 control module 250. Additionally, the server 101 may comprise server 101 data structures 270 which contain health care location (e.g., hospital or other health care facility), physician, health service category (e.g., physician specialty), and on-call schedule data. As used herein, health care location includes hospitals, urgent care centers, health care facilities, or any other location at which a patient may receive health care or medical attention, such as a doctor's office or the scene of a medical emergency where medical personnel are dispatched to the scene. Medical personnel may include doctors, nurses, paramedics, or any other person providing a medically related service. The data structures 270 may also comprise other data, such as potential transportation carrier data (i.e., companies that transport patients to hospitals and other facilities), as well as potential health-related services data, etc.

Figure 2B:
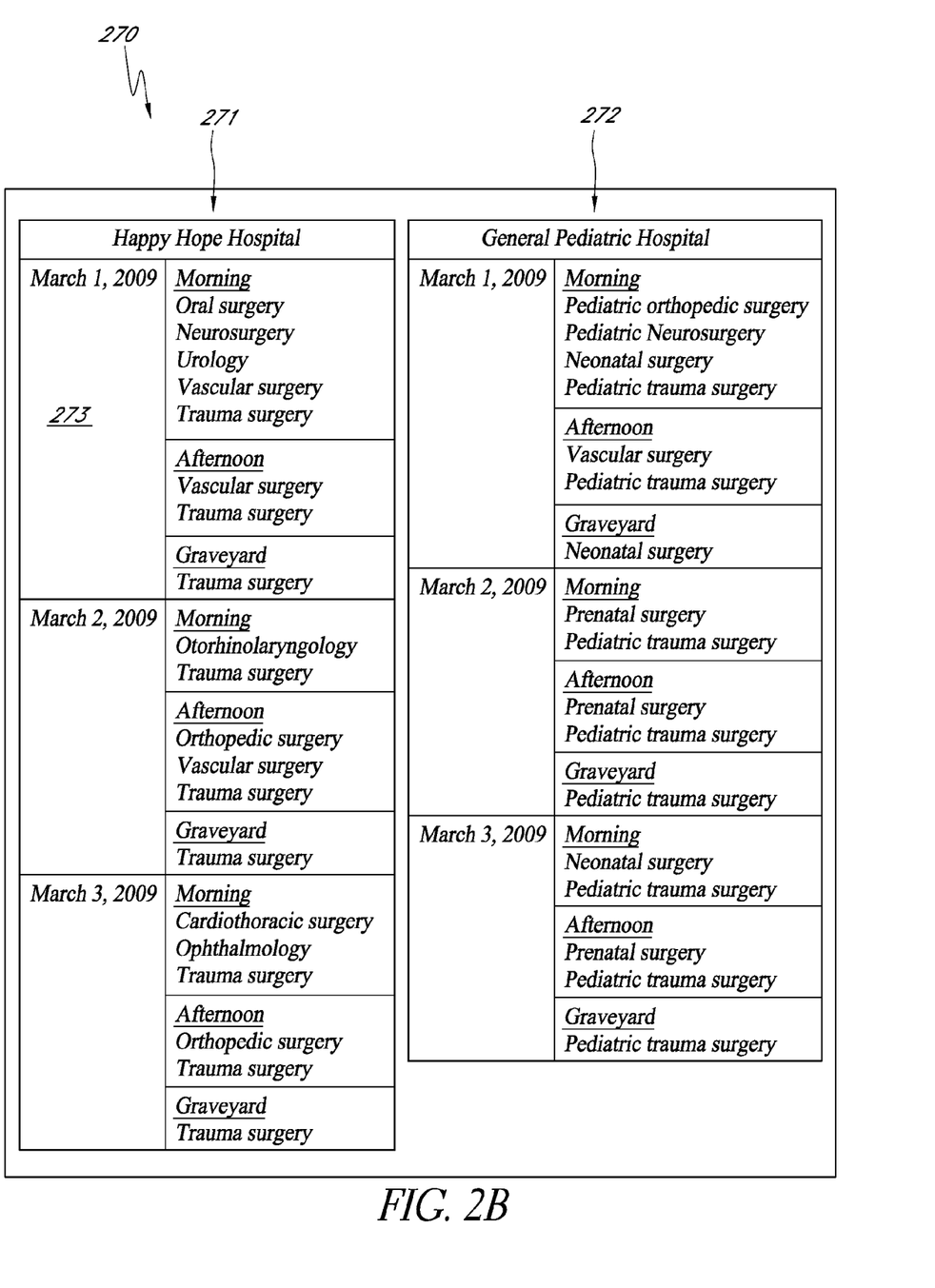
FIG. 2B schematically depicts an embodiment of a data structure containing on-call schedule data for two health care facilities.

FIG. 2B schematically depicts an embodiment of a data structure 270 containing on-call schedule data 271, 272 for two health care facilities or locations. For each health care facility, the data structure 270 may include date and time related information regarding which medical specialties are scheduled to be on-call or otherwise available at the health care facility. While only medical specialty is illustrated in FIG. 2B, it is understood that other on-call related data may be included in the on-call schedule data 271, 272, such as doctor's name, phone number, etc. As illustrated in data entry 273, a particular calendar day may be divided into several shifts and hence data may be entered on a shift basis. However, on-call schedule data may also be entered on an hourly basis.

Broadly speaking, the medical specialties indicated in FIG. 2B represent health service categories available at the two health care locations. As used herein, health service category may include a medical specialty of a physician. In some embodiments, the health service category may include the medical services of a non-physician, such as the availability of a nutritionist or a lactation consultant. In some embodiments, health service category may include other medical services, such as special medical equipment. In some embodiments, on-call schedule data 271, 272 may represent the availability of medical staff, such as a technician, to operate the special medical equipment. In some embodiments, health service category may include broad medical services, such as a labor ward. In some embodiments, the health service category may indicate that a health care location has a particular department, such as a psychiatric department.

Although not illustrated in on-call schedule data 272, 273, data structure 270 may also include physical location data (e.g., street address or other location data) for the health care facility for distance-based searching, as will be discussed further later. In some embodiments, data structure 270 may also comprise other kinds of medically related data. In some embodiments, data structure 270 may include data related to health care locations, such as medical equipment available at health care locations, the insurance carriers with whom health care locations have a contract, transportation options to health care locations, etc. Such data in data structure 270 may also be used as criteria for a search query or may be included in results to a search query, described in various embodiments below.

Figure 3:
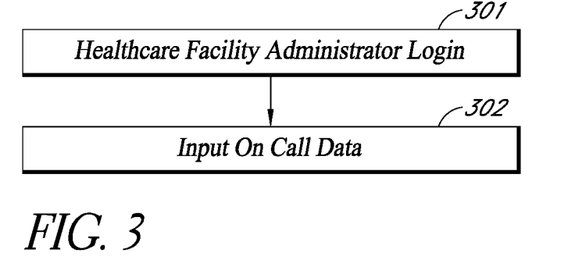
FIG. 3 schematically depicts a flow chart of an embodiment of a method of inputting on-call data.

FIG. 3 schematically depicts a flow chart of an embodiment of a method of inputting on-call schedule data 271, 272 (FIG. 2B). In the illustrated embodiment, participating health care locations, facilities, and/or institutions may have an administrator who can login 301 to a server through, for example, a website. In step 302, after login 301, the administrator may input on-call schedule data 271, 272, which may include data such as doctor name, specialty, time/date or shift doctor will be on-call, doctor contact information, etc. The administrator may input this data 302 from time to time, such as on a daily basis. Alternatively, the administrator may input this data 302 on a monthly basis or any other periodic basis. As changes to the schedule occur, the system may be configured to allow the administrator to change the on-call schedule for the administrator's facility. The data may then aid the server in retrieving the on-call schedule data on a real-time basis. Hence the server may use the entered data to answer queries seeking the nearest health care location, hospital, health care facility, or other participating institution with an on-call specialist of a particular specialty. In another embodiment, participating health care locations may send a copy of their doctor on-call schedule to a central data entry location. In this embodiment, a centralized administrator may enter the data from various health care locations from time to time or on a regular basis, for example, on a monthly basis.

In various embodiments, the administrator may input additional information other than the on-call schedule information. For example, in some embodiments, the administrator may be able to input transportation carriers that the health care location uses or prefers. In some embodiments, the administrator may be able to input data related to the medical equipment or facilities available at the health care location, e.g. MRI machine, hyperbaric chamber, or other specialized equipment related to the diagnosis and treatment of medical conditions. In some embodiments, the administrator may be able to input insurance carriers or providers with which the health care location currently has a contract or other billing relationship. In this way, when searching for a health care location, in various embodiments, a search may be conducted using any of the above data as search criteria, alone or in combination with other data.

Figure 4A:
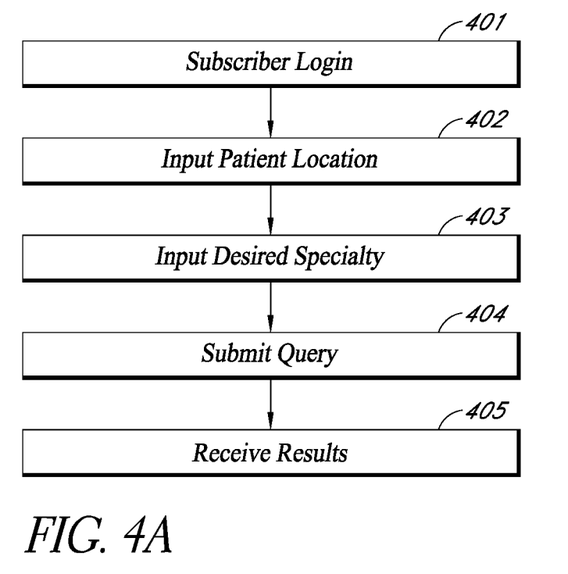
FIG. 4A schematically depicts a flow chart of an embodiment of a method of identifying a health care facility which currently has a physician on-call with a desired specialty.

FIG. 4A schematically depicts a flow chart of a method of identifying a health care location or facility which currently has a physician on-call with a desired specialty. As described above, the central server 101 (FIGS. 1, 2A) will contain a database or data structure 270 containing on-call schedule data 271, 272 for participating health care locations, such as hospitals and other health care facilities. In one embodiment, a subscriber or searcher may login 401, enter patient location or other location 402, such as an address or a zip code. The subscriber may then also input the required or desired specialty 403 and submit the query 404. In other embodiments, no login is required. In one embodiment, the server will search the database containing real-time on-call schedule data 271, 272, and return results such as the nearest hospital(s) or other health care location(s) with the desired specialty, contact information and street address (or other physical location data) for the health care location(s), name of the specialist, a map, etc. In some embodiments, a searcher may include other search criteria, such as health insurance accepted by the health care location. Hence the subscriber or searcher receives the results 405. The subscriber may query the closest hospitals within a given radius, or other similar search criteria, such as the nearest N hospitals with no distance limitation (where N may be the nearest 3, 10, or other user selected number).

It is understood that the nearest hospital may indeed be far. For example, a child in Reno, Nev. may require the medical attention or care of a pediatric neurosurgeon as soon as possible. The condition of the child may be such that the child is non-dischargeable and must remain under medical supervision until the required medical care is received. The nearest pediatric neurosurgeon currently on call may be hundreds of miles away, for example, in a pediatric hospital in northern California. In this example, the subscriber or searcher may then receive results including the address and contact information of the pediatric hospital in northern California as well as other hospitals which may be even further away. Then the doctor or other medical personnel presently attending to the child may decide to transfer the child to one of the identified locations immediately.

In some embodiments, the server 101 may also provide contact information for appropriate transportation carriers that could transport the patient from the inputted location to the identified hospital(s). For example, the server may return the contact information of a helicopter carrier capable of transporting a patient from the inputted location to the hospital identified as having a specialist on-call of the requested specialty. Similarly, the server may return the contact information of major region centers that, although further away, provide a broad range of health care services. Then the subscriber can decide on the best alternative facility given the patient's condition. The subscriber may be a hospital or other health care provider, such as a doctor's office, or other subscribing facility. The subscriber may even be a patient. For example, a patient may login to the patient's insurance carrier or provider, and request information from the insurance carrier regarding urgent care. The patient may be able to input the desired specialty, and the insurance carrier could access the server on behalf of the patient, and then provide the results to the patient. It is understood that embodiments of the system can be used to find emergent care. As used herein, emergent care can include care needed by a patient who is suffering from an emergency medical condition.

Figure 4B:
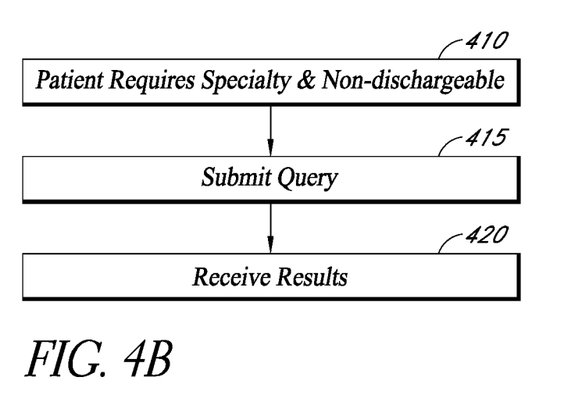
FIG. 4B schematically depicts a flow chart of an embodiment of a method of finding medical treatment for a patient.

FIG. 4B schematically depicts a flow chart of a method of finding medical treatment for a patient at a first health care location, such as in the emergency room of a hospital or at the scene of a medical emergency, such as an accident. In step 410, medical personnel may determine that the patient requires a physician of a particular specialty and that the patient is non-dischargeable. For example, after an appropriate medical screening examination, medical personnel (such as an emergency room physician) may determine that the patient is suffering from an emergency medical condition. Based on such a determination, the patient may be classified as non-dischargeable or other classification indicating that the patient is suffering from an emergency medical condition and/or requires the care of a specialist. In some embodiments, the classification may indicate that the patient requires the care of the specialist immediately, urgently, or emergently. In some embodiments, the classification may indicate that the patient requires the care of the specialist within a certain, specified time period. In view of the classification, a medical record may be made to indicate the classification. The medical record may be in any recording medium, such as paper, magnetic voice or data storage, computer-based data storage, etc. In some embodiments, a medical record may include a written note, instruction, or indication. In some embodiments, the medical record may be made by the medical personnel, or may be made by someone other than the medical personnel, upon instruction by the medical personnel. In some embodiments, the medical record may be a voice recording made by the medical personnel. In some embodiments, the medical record may be a recorded instruction to transfer a patient to a hospital with a particular specialist on call or with particular medical equipment or facilities.

Medical personnel may include doctors, such as emergency room doctors, or emergency response providers who are dispatched to the scene of a medical emergency. Medical personnel may be any health care practitioner, such as a nurse. In some cases, the medical emergency may be acute and it may be determined that the patient must be seen by or receive the medical attention of a specialist within less than one hour or even less than one half of an hour. In other cases, the medical emergency may be less acute. However, the patient may have a condition such that it is determined that the patient must remain in medical care or under medical supervision until a physician of a particular specialty examines and treats the patient. If such a physician is not available at the patient location, medical personnel may be obligated to find another (a second) health care location where such a physician of a particular specialty is currently, or soon will be, available, and transfer the patient to the second health care location. In step 415, a query is sent over an electronic network to a computer. The query may include the patient location as well as the desired specialty, e.g., the particular specialty required by the patient. In some embodiments, the query may include a certain time period such as the time within which the care of the specialist is needed, e.g., within 24 hours, 12 hours, 6 hours, 1 hour, or less than 1 hour, and/or a maximum distance from the patient's current location. In some embodiments, the query may include information related to medical equipment required by the patient, e.g., a hyperbaric chamber or other specialized equipment for diagnosing or treating a medical condition. In some embodiments, the query may include the patient's insurance carrier or provider. In some embodiments, the query may be sent by a hand held device.

In step 420, results are received for a second health care location that currently has a physician available to treat the patient at the second health care location. The results may include multiple second health care locations. In some embodiments, the results may include the distance between the patient location and the second health care location(s). Hence, in some embodiments, results for a returned health care location may include at least one time estimate for travel between the patient location and the second health care location(s). For example, in some embodiments, the results may include suggested transportation options (ambulance, helicopter, specific transportation providers, etc.) for each returned health care location and/or estimated travel time between the patient location and the second health care location based on each suggested transportation option. The transportation option may allow for transportation of the patient from the patient's location to the second health care location within said certain time period within which the care of the specialist is needed. In some embodiments, the results may include health care locations that do not currently have physicians of the required specialty on-call at the moment, but expect to have such a physician arriving soon, for example, when a physician of the desired specialty will soon be arriving at the beginning of the next shift and/or when the physician of the desired specialty will be arriving at the second health care location within the time within which the care of the specialist is needed. In some embodiments, the results may include health care locations that do not currently have physicians of the required specialty currently on call, but expect to have such a physician arriving within either the certain time period within which the care of the specialist is needed or the estimated travel time between the patient location and the second health care location. This may be indicated in the results received. For example, the results may indicate that the second health care location has the specialist currently on call. If the specialist is not currently on call, but soon will be, the results may indicate that the specialist is scheduled to arrive within a certain amount of time, e.g., in one hour or thirty minutes.

As discussed above, in step 420 (or 405 in FIG. 4A), results are received for a second health care location that currently has, or soon will have, a physician available to treat the patient at the second health care location. In various embodiments, results may include data related to transportation options, distance from patient (first health care) location, estimated travel time between patient and second health care location, data related to medical equipment available at the second health care location, and other medically relevant data relating to the facilities and capabilities of the second health care location and patient transportation to the second health care location. In some embodiments, the results in step 420 may also include insurance related data. For example, if a patient is transferred to a hospital or other health care location that does not have a contract (e.g. non-contracting health care location) with the patient's insurance provider, even if emergently transferred, the insurance provider may not be required to pay the entire bill to the non-contracting hospital. In some situations, the patient cannot be billed for the difference. In a preferred embodiment, the results may include insurance providers that presently have a contract or other billing relationship with the returned second health care location(s). Hence, in some embodiments, the results may include health insurance information related to health insurance accepted by the returned second health care location(s) in treating a patient. In some embodiments, the query submitted in step 415 (404 in FIG. 4A), may also include insurance-related information, e.g. the insurance provider of the patient and/or other insurance information. In such embodiments, the results may be limited to health care locations that accept the queried insurance carrier or the results may include both health care locations that accept the queried insurance carrier as well as non-contracting health care locations and health care locations that otherwise do not accept the queried insurance carrier.

In some embodiments the subscriber—such as a health care facility searching for an alternative nearby health care facility with a doctor currently on-call with a desired medical specialty—may be able to select one of the alternate health care facilities identified by the server 101 as having a specialist with the desired medical specialty currently on-call. The server 101 may further be configured to then electronically contact the selected health care facility to inform it of the potential transfer of the patient, and the specialized medical care required by the patient. The server 101 may further be configured to verify if the patient was indeed later transferred to the identified health care facility, or to another facility.

Over time, transfer patterns may be discernable. For example, in some embodiments the server 101 and/or system can be configured to track data related to past searches. For example, the server 101 may record data indicative of, and correlations between, patient location, the medical specialty required by the patient, the time of the query, the health care facilities identified as presently having the needed specialist, the health care facility selected for transfer, and the health care facility to which the patient is ultimately transferred. This information may include correlations between data for queried locations, queried specialties, returned health care facilities, selected health care facilities, and times of queries. More generally, the server may be configured to identify correlations between any data inputted by the subscriber in the query, and any results returned by the server. Furthermore, the server may be configured to identify correlations among the data inputted by the subscriber and correlations among the results returned by the server.

In some cases, there may be no immediately available hospitals nearby with the desired specialist on-call. In such a case, the server may additionally comprise a system to electronically contact participating nearby physicians to see if they are available to come to the subscribing facility to treat the patient. In other embodiments, the server may be able to electronically contact participating physicians who are not nearby the subscribing facility, but are nearby a regional center or other appropriate alternative facility. The mode of contact may be, for example and without limitation, a page or a text message asking the physician if he or she is available to accept the transfer of the patient to the alternative facility.

In some embodiments, the system can serve as a referral service for subscribers (e.g., patients or doctors). For example, there are times when a patient does not need an emergency transfer and can be seen in a follow up session or appointment. In this case there may be information provided in the data bank. Physicians, hospitals, and other organizations who wish to participate in the data bank may enter their information. Other subscribers who may participate in such a referral service include, for example, a subspecialist who may not be on call for a hospital currently, regional stroke centers, chest pain centers, teaching institutions, government institutions, and transportation companies to name a few.

Figure 5:
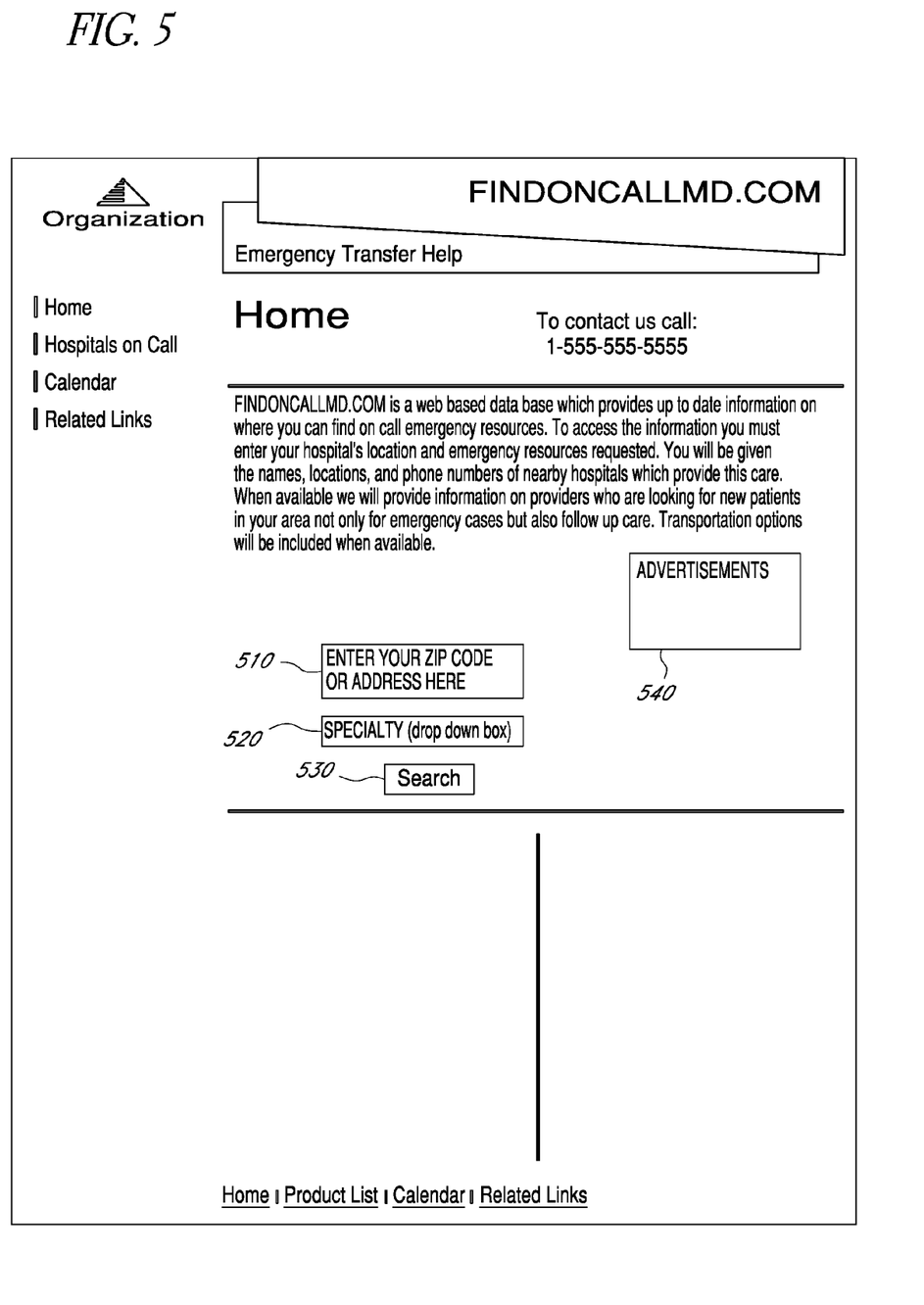
FIG. 5 shows a sample home page and an embodiment of an interface for entering address and/or location data and medical specialty data for a query.

FIG. 5 shows a sample home page and an interface for entering address and/or location data and medical specialty data for a query as discussed above in relation to FIGS. 4A and 4B. As illustrated, the home page may include a field 510 for entering the present location of the patient. This location may include the patient's home, patient's doctor's office, hospital or other health care facility at which patient is presently located, or any other location, such as the scene of a medical emergency. The home page may also include a field 520 for entering the desired specialty. Field 520 may preferably be a drop down box to allow for a standard naming convention of medical specialties, however, in some embodiments, text may also be input into field 520. The home page may also include a search button 530 to initiate the sending of the query over an electronic network to a computer or server 101 (FIGS. 1, 2A). The home page may include relevant advertisements 540, such as medical transport carriers or other relevant advertising.

Figure 6:
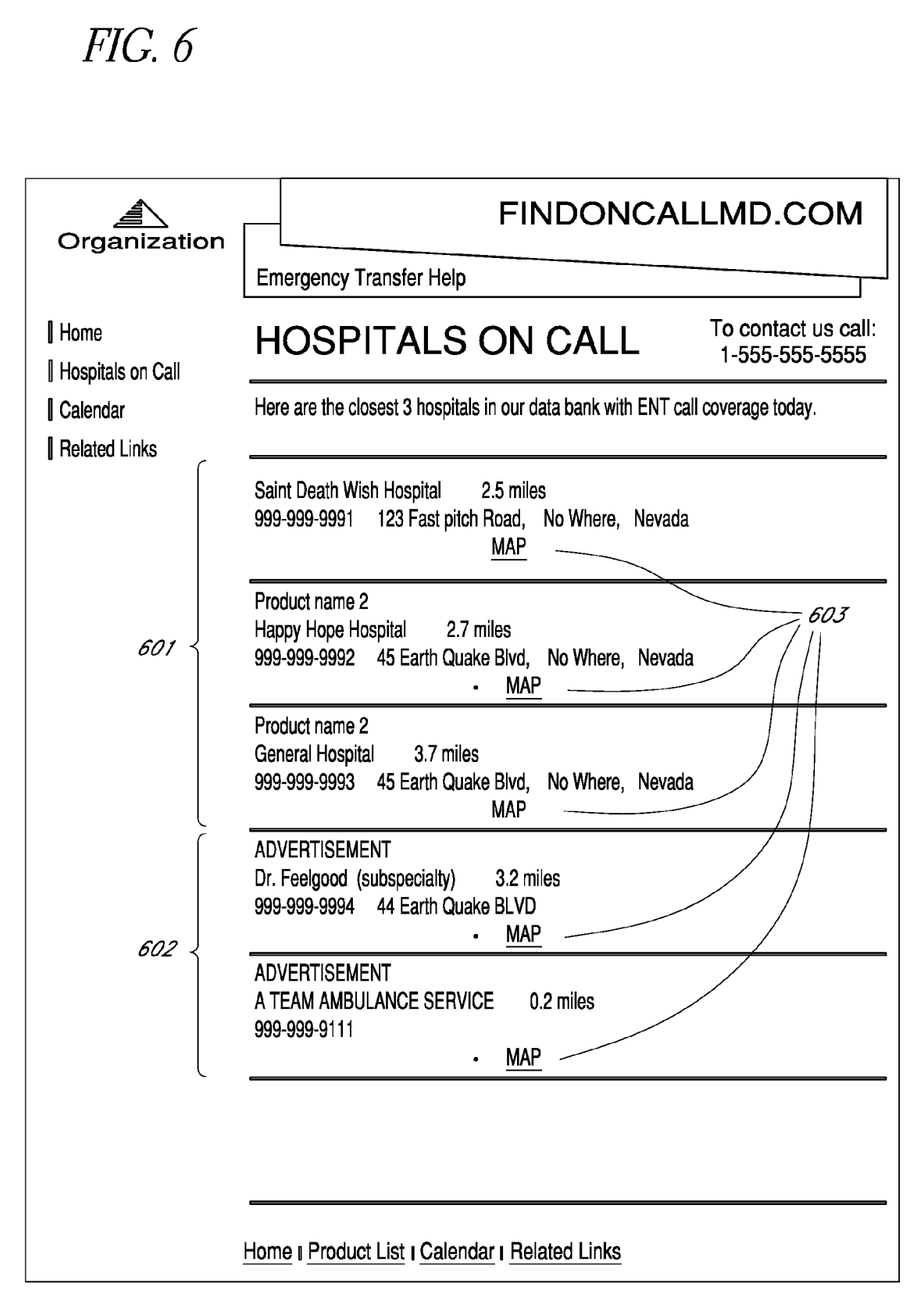
FIG. 6 shows an embodiment of a webpage with information from the data bank.

FIG. 6 shows an embodiment of the retrieved information from the data bank. In the illustrated example, a particular location in Nevada was entered with the desired specialty being an ear-nose-throat specialist (ENT). The results 601 include three health care locations (e.g., hospitals) with an ENT specialist currently on-call to care for the patient. As illustrated, the results 601 include the distance between the entered location and the identified health care location. In the illustrated embodiment, clicking on a "MAP" hyperlink 603 related to a health care location brings up a map of the health care location and/or directions from the entered location and the health care location. Relevant advertising 602 may also be displayed, for example, an advertisement for a doctor of the desired specialty or an ambulance service.

Figure 7:
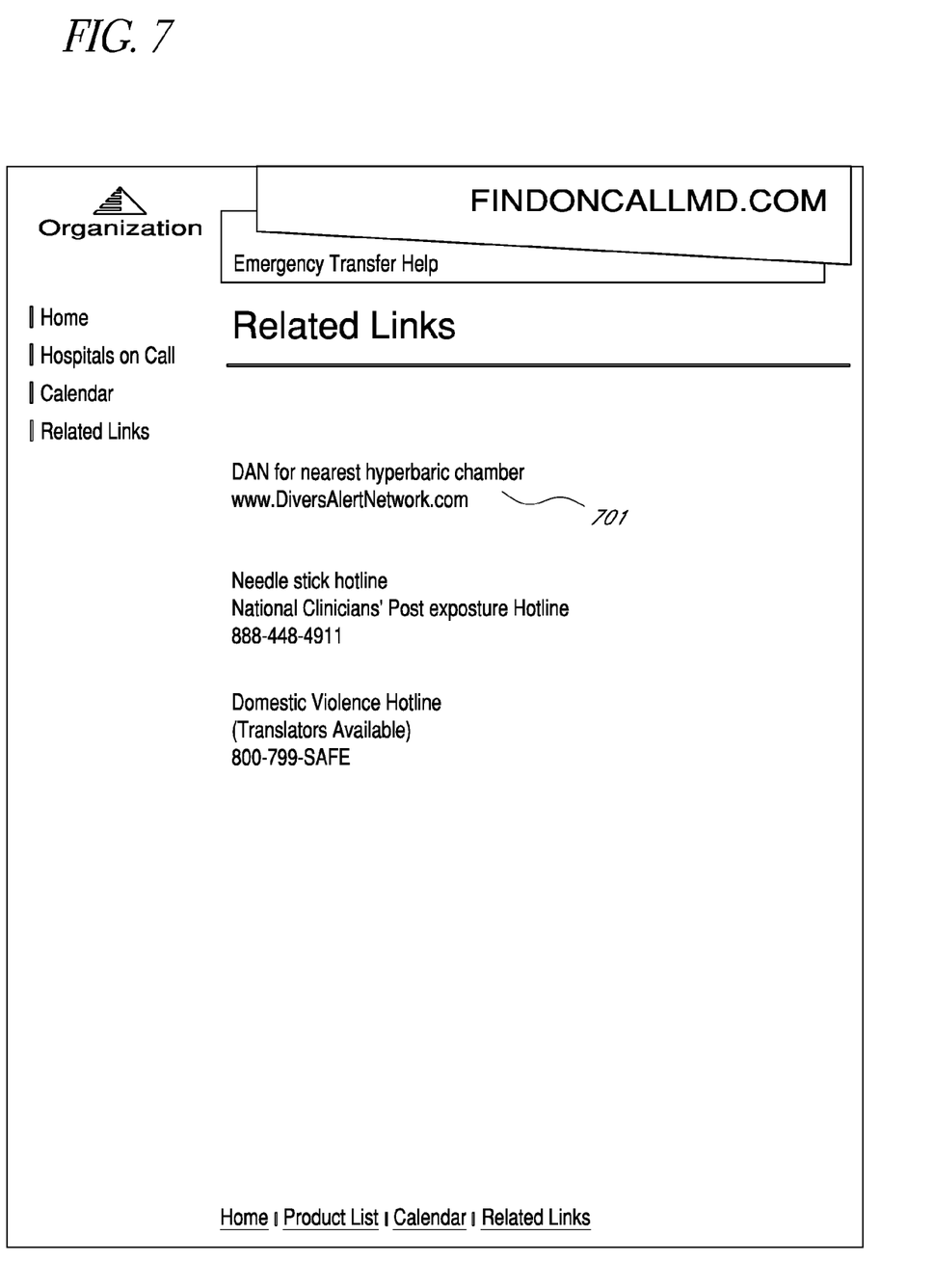
FIG. 7 shows related links available for the user's perusal in accordance with an embodiment of the invention.

FIG. 7 shows related links 701 available for the user's perusal. For example, a website may include a webpage with relevant links 701 to other services. For example, the website may be used as a medical services portal for other related searches and may include a link to search for the nearest location with particular medical equipment, such as a hyperbaric chamber or an MRI machine.

Figure 8:
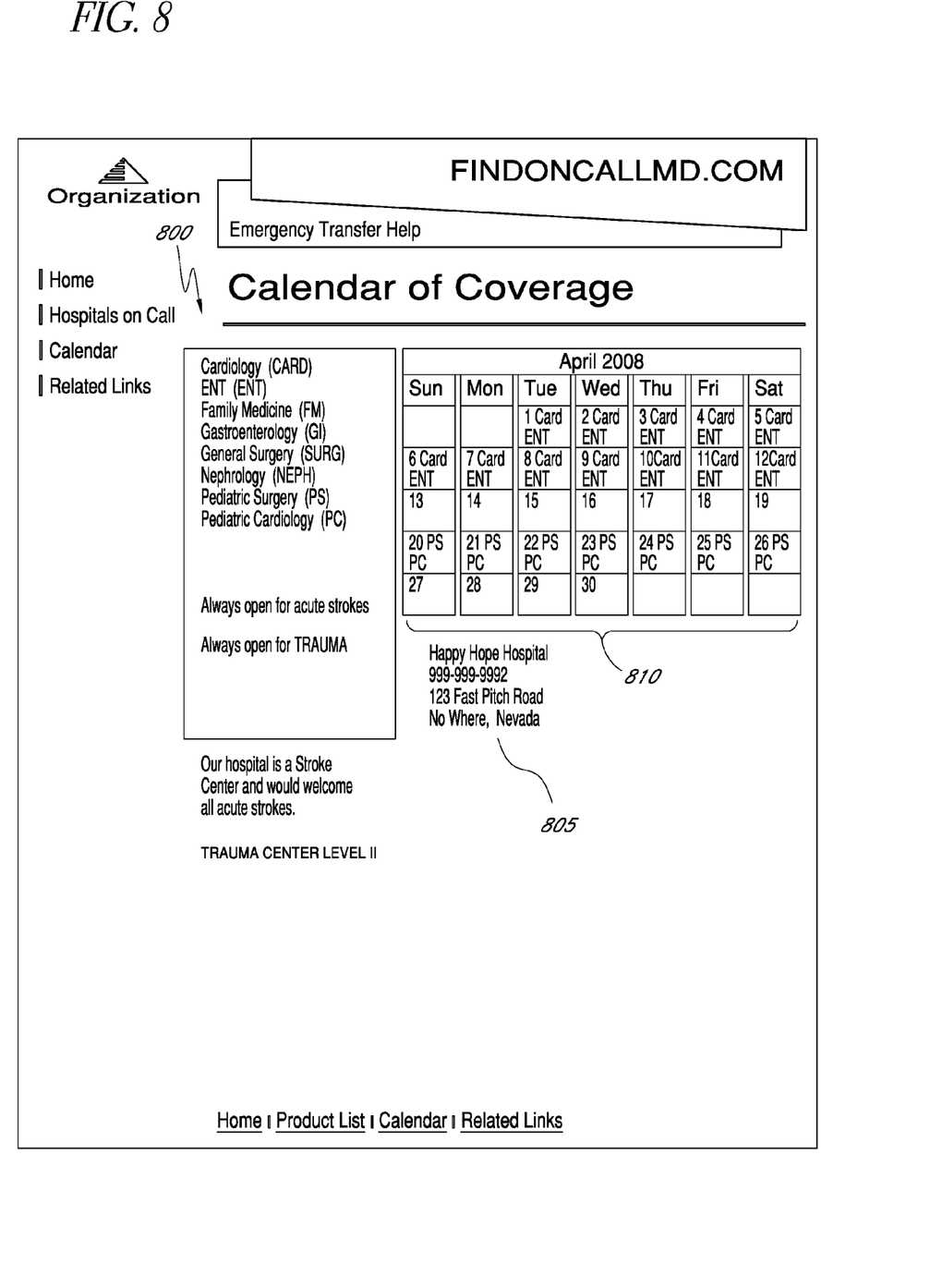
FIG. 8 is an embodiment of a data collection tool used to collect on-call schedule data for the queriable data bank.

FIG. 8 is a sample of a data collection tool 800 used to collect on-call schedule data 271, 272 for the queriable data bank, as discussed above in relation to FIGS. 2A, 2B and 3. An administrator associated with a particular participating health care location 805 such as a hospital, urgent care facility, or other health care facility may log into a website to input data into the server 101 to be included in the on-call database. The website may then direct the administrator to a data collection tool 800 as shown in FIG. 8. The tool 800 may include a calendar 810. The calendar 810 may then be populated with the specialties of the physicians scheduled to be on-call at the participating health care location 805. As illustrated, the administrator has selected a month (April 2008). For example, the administrator may further select a particular day in the month, and the day may then be divided into time shifts, as shown in FIG. 2B. The time shifts may be hourly or even greater time resolution is possible. Each participating health care location 805 may have particular settings preferences, such as its on-call shift structure preference. In this way, when accessing data collection tool 800, an administrator for one participating health care location 805 may see, e.g. three shifts per day requiring population with specialty information, while an administrator for another participating health care location 805 may see, e.g. two or four, depending on the preference settings for the particular health care locations. Furthermore, the tool 800 may be customizable in other ways.

For example, the administrator for each participating health care location 805 may be able to upload information relating to all physicians who are affiliated with the location 805. In this way, the administrator may only need to enter data relating to each individual physician and when that physician will be on call. The tool 800 can then automatically correlate the data input by the administrator to specialty related on-call data.

Although certain preferred embodiments and examples are discussed herein, it is understood that the inventive subject matter extends beyond the specifically disclosed embodiments to other alternative embodiments and/or uses of the invention and obvious modifications and equivalents thereof. It is intended that the scope of the inventions disclosed herein should not be limited by the particular disclosed embodiments. Thus, for example, in any method or process disclosed herein, the acts or operations making up the method/process may be performed in any suitable sequence and are not necessarily limited to any particular disclosed sequence. Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

The invention claimed is:

1. A system for delivering on-call schedule information for medical specialist health care providers available to treat a patient in need of emergency medical care, comprising:
    a machine-readable database comprising on-call schedule information for a plurality of non-emergency medicine specialist physician health care providers currently on-call and available to physically treat the patient for an emergent medical condition, and locations of health care facilities with which said health care providers are affiliated; and
    a server computer system configured to electronically receive a query comprising a health service category and a location of a patient in need of emergency medical care by a non-emergency medicine medical specialist physician, the computer system configured to respond to the query by searching the database to find at least one health care facility having a non-emergency medicine medical specialist physician health care provider who is currently on-call and currently available to physically treat the patient and accept the patient for potential transfer to the health care facility, the health care provider having expertise in said health service category, said health care facility being within a certain distance of said patient location, wherein the computer system is configured to output an identification and location of the health care facility found by searching the database.

2. The system of claim 1, wherein said query specifies said certain distance.

3. The system of claim 1, further comprising a plurality of client computer systems each configured to send the query to the server computer system over an electronic network.

4. The system of claim 3, wherein the server computer system is configured to respond to the query by sending an identification and location of the health care facility found by searching the database to a client computer system that sent the query to the server computer system, said client computer system configured to allow a user to select the health care facility for receiving a patient currently requiring care from said affiliated health care provider.

5. The system of claim 4, wherein the server computer system is configured to respond to a selection of the health care facility by a user of the client computer system by sending an electronic notification of said selection to said selected health care facility.

6. The system of claim 4, wherein the server computer system is configured to respond to a selection of the health care facility by a user of the client computer system by storing said selection in a database of health care facility selections.

7. The system of claim 3, wherein the server computer system is configured to receive a plurality of queries from at least one of said client computer systems, each query comprising a health service category and a location of a patient in need of emergency medical care, the server computer system being configured to respond to each query by sending an identification and location of one or more health care facilities found, if any, by searching the database to the at least one of said plurality of client computer systems that sent the query to the server computer system, said client computer systems each configured to allow a user to, select one of the health care facilities, the server computer system being configured to record, for each of said queries, (1) the health service category of the query, (2) the patient location of the query, (3) a time of the query, (4) one or more health care facilities, if any, found by searching the database in response to the query, and (5) one or more selections, if any, of said health care facilities whose identifications were sent to the at least one of said client computer systems that sent the query to the server computer system.

8. The system of claim 3, wherein the network comprises the Internet.

9. The system of claim 1, wherein the database includes contact information for the health care facilities and/or health care providers, the server computer system configured to output contact information of the health care facility found by searching the database.

10. The system of claim 1, wherein the server computer system is configured to receive on-call schedule information for the health care providers over an electronic network, the server computer system configured to update the database with the received on-call schedule information.

11. The system of claim 1, wherein the database includes contact information for patient transporters, the server computer system configured to respond to the query by:
    searching the database to find at least one patient transporter that can transport a patient from the patient location to the health care facility found by searching the database; and
    sending contact information for said found patient transporter to a client computer system that sent the query to the server computer system.

12. A method of identifying a health care facility that is able to render emergency medical care by a medical specialist physician, comprising:
    sending a query over an electronic network to a server computer, said query including a health service category and a location of a patient in need of emergency medical care by a non-emergency medicine medical specialist physician; and
    receiving over the network an identification and location of a health care facility having a medical specialist physician health care provider who is currently on-call and currently available to physically treat the patient and accept the patient for possible transfer to the health care facility, the health care provider having expertise in said health service category;

wherein the method is performed by one or more computing devices.

13. The method of claim 12, wherein the query includes a specification of a certain distance, the health care facility being within the certain distance of the patient location.

14. The method of claim 12, further comprising selecting the received health care facility from a screen display.

15. The method of claim 12, further comprising receiving contact information of the health care facility over the network.

16. The method of claim 12, further comprising receiving contact information for a patient transporter that can transport a patient from the patient location to the health care facility.

17. The method of claim 12, wherein said receiving comprises:
   receiving over the network identifications and locations of a plurality of health care facilities each having a health care provider who is currently on call and currently available to physically treat the patient, each of the health care providers having expertise in said health service category; and
   receiving over the network, for one or more of the health care facilities, a transportation option for transporting the patient from the patient location to the health care facility.

18. The method of claim 17, wherein each transportation option comprises:
   at least one carrier for transporting the patient from the patient location to the health care facility; and
   for each carrier, a time estimate for said transporting the patient.

19. The method of claim 12, wherein said receiving comprises:
   receiving over the network identifications and locations of a plurality of health care facilities each having a health care provider who is currently on call and currently available to physically treat the patient, each of the health care providers having expertise in said health service category; and
   receiving over the network, for one or more of the health care facilities, health insurance information related to health insurance accepted by the one or more health care facilities in treating a patient.

20. A method of providing health care facility information, comprising:
   receiving a query comprising a health service category and a location of a patient in need of emergency medical care, the medical care needed from a non-emergency medicine medical specialist physician; and
   searching a machine-readable database comprising on-call schedule information for a plurality of health care providers, and locations of health care facilities with which the health care providers are affiliated;
   wherein searching the database comprises finding at least one health care facility having a health care provider who is currently on-call and currently available to physically treat the patient and accept the patient for possible transfer to the health care facility, the health care provider having expertise in said health service category, said health care facility being within a certain distance of the patient location;
   wherein the method is performed by one or more computing devices.

21. The method of claim 20, further comprising sending an identification and location of the health care facility found by searching the database to a client computer system from which the query was received.

22. The method of claim 21, further comprising responding to a selection of the health care facility by a user of the client computer system by sending an electronic notification of the selection to the selected health care facility.

23. The method of claim 21, further comprising responding to a selection of the health care facility by a user of the client computer system by storing the selection in a database of health care facility selections.

24. The method of claim 20, wherein receiving the query comprises receiving a specification of said certain distance.

25. The method of claim 20, further comprising:
   receiving a plurality of queries each comprising a health service category and a location of a patient in need of emergency medical care;
   responding to each query by searching the database to find at least one health care facility having a health care provider who is currently on-call and currently available to physically treat the patient, the health care provider having expertise in the health service category of the query, the health care facility found in response to the query being within a certain distance of said patient location of the query;
   for each query, sending an identification and location of the health care facility found by searching the database to a client computer system from which the query was received; and
   recording, for each of said queries, (1) the health service category of the query, (2) the patient location of the query, (3) a time of the query, (4) one or more health care facilities found by searching the database in response to the query, and (5) one or more selections, if any, of said health care facilities by users of the client computer systems.

26. The method of claim 20, wherein said database includes contact information for the health care facilities and/or health care providers, the method further comprising sending contact information of the health care facility found by searching the database to a client computer system from which the query was received.

27. The method of claim 20, further comprising:
   receiving on-call schedule information for the health care providers over an electronic network; and
   updating the database with the received on-call schedule information.

28. The method of claim 20, wherein the database includes contact information for patient transporters, the method further comprising responding to the query by:
   searching the database to find at least one patient transporter that can transport a patient from the patient location to the health care facility found by searching the database; and
   sending contact information for said found patient transporter to a client computer system from which the query was received.

29. A method of finding a higher level of medical treatment for a patient at a first health care location for potential transfer of the patient to a second health care location, the method comprising:
   performing a medical screening examination of a patient;
   determining, based on the examination, that the patient is in need of additional emergency medical care and is non-dischargeable until such emergency medical care is received and that the additional emergency medical care is not available at the first health care location;

sending a query over an electronic network to a server computer system, the query including a medical specialty and the first health care location; and receiving over the network a second health care location within a certain distance of the first health care location, wherein a physician of the medical specialty is currently available to physically treat the patient at the second health care location or will be available to physically treat the patient at the second health care location within six hours and provide the additional emergency medical care not available at the first health care location;

wherein the sending and receiving steps are performed by one or more computing devices.

30. The method of claim 29, further comprising making a medical record for the patient, the medical record indicating that the patient is non-dischargeable until the patient receives attention from a physician of the specialty.

31. The method of claim 30, wherein the medical record indicates that the patient should receive attention from the physician of the particular specialty within a certain time period.

32. The method of claim 31, further comprising receiving a transportation option that allows for transportation of the patient from the first health care location to the second health-care location within said certain time period.

33. The method of claim 31, wherein the query specifies the certain time period.

34. The method of claim 29, wherein one of the first health care location and the second health care location comprises a hospital.

35. The method of claim 29, wherein the first health care location comprises a scene of a medical emergency.

36. The method of claim 29, wherein sending the query over the electronic network comprises specifying said certain distance.

37. The method of claim 29, further comprising receiving over the network, for the second health care location, health insurance information related to health insurance accepted by the second health care location in treating the patient.

* * * * *